United States Patent [19]

Giroux

[11] 4,439,443

[45] Mar. 27, 1984

[54] SNAKE BITE THERAPY

[75] Inventor: Eugene L. Giroux, Cincinnati, Ohio

[73] Assignee: Richardson-Merrell Inc., Wilton, Conn.

[21] Appl. No.: 394,967

[22] Filed: Jul. 2, 1982

Related U.S. Application Data

[60] Division of Ser. No. 290,906, Aug. 7, 1981, Pat. No. 4,347,255, which is a continuation of Ser. No. 140,446, Apr. 17, 1980, abandoned.

[51] Int. Cl.$^3$ .................... A61K 31/34; A61K 31/38; A61K 31/40
[52] U.S. Cl. .................................. 424/285; 424/275; 424/274
[58] Field of Search .................. 424/285, 274, 275

[56] References Cited

U.S. PATENT DOCUMENTS

| | | | |
|---|---|---|---|
| 4,130,653 | 12/1978 | Giroux et al. | 424/285 |
| 4,169,149 | 9/1979 | Giroux et al. | 424/274 |
| 4,210,665 | 7/1980 | Giroux et al. | 424/275 |
| 4,226,882 | 10/1980 | Giroux et al. | 424/285 |
| 4,347,255 | 8/1982 | Giroux | 424/285 |

Primary Examiner—Albert T. Meyers
Assistant Examiner—John W. Rollins, Jr.
Attorney, Agent, or Firm—Stephen L. Nesbitt; William J. Stein

[57] ABSTRACT

A method of reducing local hemorrhage and tissue necrosis resulting from the bite or sting of a venomous animal whereby an envenomated mammal is treated with a compound of the formula

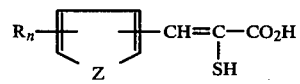

or a corresponding disulfide wherein n is 1, 2 or 3; Z is O, S or NH; R is H, a straight or branched chain lower alkyl group of from 1 to 4 carbon atoms, hydroxy, a straight or branched chain lower alkoxy group of from 1 to 4 carbon atoms, fluoro, chloro, bromo, iodo or trifluoromethyl; or a pharmaceutically acceptable salt thereof.

6 Claims, No Drawings

SNAKE BITE THERAPY

This is a divisional of copending application Ser. No. 290,906, filed Aug. 7, 1981, now U.S. Pat. No. 4,347,255, which is a continuation of copending application Ser. No. 140,446 filed Apr. 17, 1980, now abandoned.

BACKGROUND OF THE INVENTION

1. Field of Invention

This invention relates to the treatment of local hemorrhage and tissue necrosis resulting from snake bite by the administration of α-mercapto-β-aryl acrylic acids and the corresponding disulfides as well as their pharmaceutically acceptable salts.

2. DESCRIPTION OF THE PRIOR ART

Venomous bites and stings, particularly venomous snake bites, result in tens of thousands of deaths each year worldwide primarily in under-developed countries. In developed countries where access to medical facilities and subsequent treatment with antivenom is readily available, death resulting from snake envenomation is rare. Although antivenom therapy is largely successful in reducing the mortality associated with venomous snake bites, it is less effective in reducing local hemorrhage and tissue necrosis, prominent symptoms of envenomation. Frequently the local tissue necrosis subsequent to a snake bite may be so severe as to result in permanent disfigurement, impairment or, in extreme cases, loss of an affected extremity.

Venom of poisonous snakes, and other venomous animals, is comprised largely or completely of a complex enzymatic mixture. In hemorrhagic factors of snake venom, those enzymes which are responsible for hemorrhagic activity, have been found to be metal dependent. Elimination of Ca (II), Mg (II) and Zn (II) from these hemorrhagic factors by various metal chelators in vitro eliminates the hemorrhagic activity, Tu, A. T., Venoms: Chemistry and Molecular Biology, John Wiley & Sons, New York (1977). See also Bjarnason, J. B. and Tu. A. T., Biochemistry 17 (16) 3395 (1978); Ownby, C. L. et al., *J. Clin. Pharm.*, 15 419 (1975); Friederick, C., and Tu., A. T., *Biochem. Pharm.* 20 1549 (1971).

Thus, a mixture of diethylenetriaminepentaacetic acid (DTPA) and procaine when injected within 15 minutes of envenomation or ethylenediaminetetraacetic acid (EDTA) when injected within 30 minutes of envenomation by snake in the vicinity of the bite is known to reduce local hemorrhage; however, these agents are without effect in reducing tissue necrosis or lethality. Ownby, C. L., et al., supra. Holvey, D. N., ed., The Merck Manual of Diagnosis and Therapy, 13th Edition, Merck Sharp and Dohme Research Laboratories, Rahway, N.J., 1972, page 1987. Moreover, EDTA is contraindicated in the presence of a disturbed electrolyte balance, a condition not uncommon with many snake bite victims. At present no agent is known to be topically effective against the local hemorrhage and tissue necrosis caused by envenomation.

Mercapto acrylic acids and their disulfides are known to be potent inhibitors of various metal dependent enzymes. Wagner, J., et al., *Can. J. Chem.*, 55, 4028 (1977). However, their utility as topically effective agents useful in reducing local hemorrhage and tissue necrosis resulting from snake envenomation, as described below, is quite unexpected.

The mercaptoacrylic acids and their corresponding disulfides are additionally disclosed at Rovazoni, C. et al., Ann. Chim. (Rome) 52, 305–12 (1962), Chem. Abstr. 57:9833 g; Haskel, et al., J. Med. Chem. 13, 697 (1970); Halestrap. A., Biochem. J. 148(1), 85 (1975) as well as in U.S. Pat. Nos. 4,124,718; 4,130,653; 4,169,149; 4,210,664; 4,210,665; and 4,226,882.

BRIEF SUMMARY OF INVENTION

This invention relates to a method of reducing local hemorrhage and tissue necrosis resulting from the bite or sting of venomous animals which comprises administering to an envenomated mammal a compound of structure 1 as well as a corresponding disulfide:

Formula 1 wherein Z is O, S or NH; R is H, methyl, ethyl, hydroxy, methoxy, ethoxy, fluoro, chloro, bromo, iodo, or trifluoromethyl; n is 1, 2 or 3; or a pharmaceutically acceptable salt thereof.

DETAILED DESCRIPTION OF INVENTION

It is apparent from the foregoing general Formula 1 that the compounds employed in the present invention are α-mercapto-β-furylacrylic acids, α-mercapto-β-thienylacrylic acids, α-mercapto-β-pyrrylacrylic acids as well as the corresponding disulfides of general Formula 2 which are α,α'-dithiobis(β-furylacrylic acids), α,α'-dithiobis(β-thienylacrylic acids), and α,α'-dithiobis(β-pyrrylacrylic acids) and the pharmaceutically acceptable salts thereof.

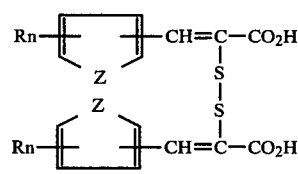

Formula 2

Pharmaceutically acceptable salts of the compounds of general Formula 1 or their corresponding disulfides of general Formula 2 shall be taken to mean a non-toxic alkali metal such as sodium or potassium; alkaline earth metal such as calcium or magnesium; ammonium ion or organic ammonium ion such as tetramethylammonium ion, carboxylic acid salt.

As used herein, the term a straight or branched chain lower alkyl group of from 1 to 4 carbon atoms is taken to mean methyl, ethyl, n-propyl, isopropyl, n-butyl and isobutyl.

As used herein, the term a straight or branched chain lower alkoxy group of from 1 to 4 carbon atoms is taken to mean methoxy, ethoxy, n-propoxy, isopropoxy, n-butoxy and isobutoxy.

The preferred compounds of this invention are those compounds of formula 1 and their disulfides wherein R is H, methyl, ethyl, hydroxy, methoxy, ethoxy, fluoro, chloro, bromo, iodo or trifluoromethyl; Z is O, S, or NH; n is 1; and their pharmaceutically acceptable salts.

Still more preferred compounds of this invention are those compounds of formula 1 and their disulfides wherein Z is O, S, or NH and R is H.

The most preferred compounds of this invention are α-mercapto-β-(2-furyl)acrylic acid and α,α'-dithiobis[β-(2-furyl)acrylic acid].

As examples of compounds of general Formula 1 and the disulfides thereof there may be mentioned the following:

α-mercapto-β-(2-furyl)acrylic acid;
α-mercapto-β-(5-trifluoromethyl-2-furyl)acrylic acid;
α-mercapto-β-(3-thienyl)acrylic acid;
α-mercapto-β-(2-pyrryl)acrylic acid;
α,α'-dithiobis[β-(2-furyl)acrylic acid]; and
α,α'-dithiobis[β-(2-thienyl)acrylic acid].

The compounds of this invention may be prepared according to the general method described by Campaigne, E. and Cline, P. E., *J. Org. Chem.*, 21, 32 (1956) by condensing the corresponding carboxaldehyde of general formula 3 with rhodanine of formula 4 and subsequently splitting the products (5) in alkaline medium, according to the general reaction scheme:

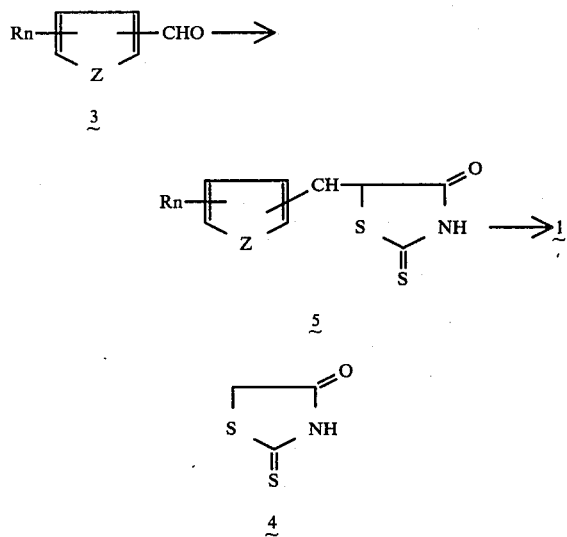

wherein in general Formulas 1, 3, 4 and 5 n is 1, 2, or 3; Z is O, S or NH; and R is H, a straight or branched chain lower alkyl group of from 1 to 4 carbon atoms, hydroxy, a straight or branched chain lower alkoxy group of from 1 to 4 carbon atoms, fluoro, chloro, bromo, iodo, or trifluoromethyl.

Where the disulfides of general Formula 1 are desired, they may be prepared by the general methods described by Campaigne, E. and Cline, P. E., supra, by oxidation of the corresponding acrylic acid of Formula 1 with iodine in alcohol or moist carbon tetrachloride or by oxidation with an organic peroxide such as benzoyl peroxide in benzene.

The desired salts may be prepared in the usual manner by reaction between a compound of formula 1 or a disulfide thereof and pharmaceutically acceptable alkali metal, alkaline earth metal, transition metal, ammonium or organic ammonium basic salt, for example, an alkoxide such as sodium methoxide or sodium ethoxide; a phenoxide such as sodium phenoxide; a hydroxide such as sodium hydroxide, potassium hydroxide or ammonium hydroxide; or a carbonate such as sodium carbonate, potassium carbonate, zinc carbonate, magnesium carbonate or sodium hydrogen carbonate.

The compounds of general Formula 1 and the corresponding disulfides wherein n is 1, 2 or 3; Z is O, S, or NH;and R is H, a straight or branched chain lower alkyl group of from 1 to 4 carbon atoms, hydroxy, a straight or branched chain lower alkoxy group of from 1 to 4 carbon atoms, fluoro, chloro, bromo, iodo, or trifluoromethyl, are useful in reducing local hemorrhage and tissue necrosis resulting from envenomation of mammals by the bite or sting of venomous animals. The compounds of the invention also appear to inhibit other poisonous factors of snake venom, particularly when administered parenterally. The compounds described herein are superior to other agents which are known to inhibit the hemorrhagic factors of venom in that they are topically effective. Accordingly, non-medically trained personnel could initiate topical treatment of a venomous bite or sting immediately after envenomation.

As used herein the term mammals is taken to mean primates including humans, sheep, horses, bovine cows and bulls, pigs, dogs, cats, rats and mice.

The term venomous animals is taken to mean venomous snakes such as pit vipers including Agkistrodon spp., Bothrops spp., Crotalus spp., Trimeresurus spp., *Lachesis mutus,* and Sistrurus spp. and vipers including Bitis spp., Causus spp., Cerastes spp., *Echis carinatus, Pseudocerastes persicus* and Vipera spp.; as well as spiders, gila monsters, centipedes, maggots, marine animals and other venomous animals whose bite or sting produces local hemorrhage and tissue necrosis.

The term venom is intended to encompass any poisonous substance which is parenterally transmitted, that is subcutaneously or intramuscularly transmitted, by the bite or sting of a venomous animal into a mammal and which contains various toxins such as hemotoxins, hemagglutinins, neurotoxins, leukotoxins, and endotheliotoxins. For the purposes of this invention, the ill-effects of a venom must include local hemorrhage and tissue necrosis. Any mammal which has been injected with a venom by the bite or sting of a venomous animal is said to be an envenomated mammal.

The term antivenom is intended to encompass an antitoxin used in the treatment of the poisonous effects resulting from the bite or sting of a venomous animal. Antivenom is generally produced by the hyperimmunization of horses and is commonly available in a lyophilized state. Administration of such antitoxin to an envenomated mammal requires parenteral injection by highly skilled medical personnel unlike the topical administration of the compounds of this invention.

In practicing the present invention the compounds of Formula 1 and their disulfides as well as the pharmaceutically acceptable salts thereof are administered to an envenomated mammal either alone, in combination with one another, or in combination with other agents known to be useful in snake bite therapy such as "antivenom." The compounds of this invention can be administered either orally; parenterally, for example, subcutaneously or intravenously; or preferably topically.

The compounds of Formula 1 can be formulated for oral administration as solid or liquid unit dosage forms. The solid dosage forms can be, for example, tablets, coated or uncoated; capsules, hard or soft; powders, granules; or pills. For solid administration the active ingredients can be combined with carriers, for example, binders such as acacia, corn starch, or gelatin; disintegrating agents such as corn starch, guar gum, potato starch, or alginic acid; lubricants such as stearic acid or magnesium stearate and inert fillers such as lactose, sucrose or corn starch. Liquid oral compositions can be, for example, dispersion, suspensions, elixirs, syrups, or simple solutions in aqueous vehicle. For liquid administration the active ingredient can be combined with a sterile liquid, for example, an oil such as peanut oil, sesame oil, cottonseed oil, corn oil or olive oil; a fatty acid such as oleic acid, stearic acid or isostearic acid; a fatty acid ester such as ethyl oleate, isopropyl myristate, fatty acid glycerides, or acetylated fatty acid glycerides; an alcohol such as ethanol, isopropanol, hexadecyl alcohol, glycerol, or propylene glycol; a glycerol ketal such as 2,2-dimethyl-1,3-dioxolane-4-methanol; an ether such as poly(ethyleneglycol)400; a petroleum hydrocarbon such as mineral oil or petrolatum; water; or with mixtures thereof; with or without the addition of a pharmaceutically suitable surfactant, suspending agent, or emulsifying agent such as pectin, carbomers, methyl cellulose, hydroxypropyl cellulose or carboxymethyl cellulose as well as buffers and preservatives. Oral compositions may also contain coloring and flavoring agents.

| Ingredients of a Tablet Formulation | | |
|---|---|---|
| | | Per Tablet |
| (a) | α-Mercapto-β-(2-furyl)acrylic acid | 100 mg |
| (b) | Cornstarch | 15 mg |
| (c) | Lactose | 33.5 mg |
| (d) | Magnesium stearate | 1.5 mg |

For parenteral administration the compounds can be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, sesame oil, soybean oil, and mineral oil. In general, water, saline, aqueous dextrose and related sugar solutions, ethanol and glycols such as propylene glycol or polyethylene glycol are preferred liquid carriers for injectable solutions.

| Preparation of a Parenteral Formulation | | |
|---|---|---|
| (a) | α,α'-Dithiobis[β-(2-thienyl)acrylic acid] | 1.000 g |
| (b) | Polyoxyethylene sorbitan mono oleate | 2.000 g |
| (c) | Sodium chloride | .128 g |
| (d) | Sterile water for injection qs ad | 20.000 ml |

The compounds of Formula 1 can be formulated for topical administration as for example, an ointment, cream, lotion, suspension, solution, gel, dusting powder, aerosol or spray. For administration as a powder the active ingredient can be combined with a carrier such as corn starch, potato starch, lactose or sucrose. For administration as an ointment, cream, lotion, suspension, solution or gel the active ingredient can be combined with an oil such as peanut oil, sesame oil, cottonseed oil, corn oil, or olive oil; a fatty acid such as oleic acid, stearic acid, or isostearic acid; a fatty acid ester such as ethyl oleate, isopropyl myristate, fatty acid glycerides, or acetylated fatty acid glycerides; an alcohol such as ethanol, isopropanol,hexadecyl alcohol, glycerol, or propylene glycol; a glycerol ketal such as 2,2-dimethyl-1,3-dioxolane-4-methanol; an ether such as poly(e-thyleneglycol)400; a petroleum hydrocarbon such as mineral oil or petrolatum; water; silicones such as methylphenylpolysiloxane; or with mixtures thereof; with or without the addition of a pharmaceutically suitable surfactant, suspending agent, or emulsifying agent such as pectin, carbomers, methyl cellulose, hydroxypropyl cellulose or carboxymethyl cellulose as well as buffers and preservatives. For administration as an aerosol or spray the compounds of this invention can be combined with solvents, buffers, surfactants, perfumes, antimicrobial agents, antioxidants and propellants. Such compositions can be applied by means of a propellant under pressure or can be applied by means of a compressible plastic spray bottle, a nebulizer or an atomizer without the use of a gaseous propellant.

| Preparation of a Topical Formulation | | |
|---|---|---|
| (a) | α-Mercapto-β-(2-thienyl)acrylic acid | 10 g |
| (b) | Ethanol | 90 g |

The amount of compound administered will vary over a wide range depending upon the mammal to be treated and the severity of the local hemorrhage and tissue necrosis and can be any amount effective in reducing local hemorrhage and tissue necrosis in envenomated mammals. A local hemorrhage and tissue necrosis reducing amount can be from about 10 mg/kg to 1000 mg/kg preferably from about 25 mg/kg to about 250 mg/kg of body weight of the mammal per day. For example, a unit dosage form may suitably contain about 1 mg to 100 mg of active ingredient as represented by Formula 1 or a corresponding disulfide as well as a salt thereof.

The following specific examples further illustrate the preparation and use of compounds employed in the instant invention.

EXAMPLE 1

α-Mercapto-β-(5-trifluoromethyl-2-furyl)acrylic acid

In a three necked flask, a mixture of 3.4 g of 5-trifluoromethyl-2-furfural, 2.92 g of rhodanine and 5.16 g of dry sodium acetate in 35 ml of glacial acetic acid is stirred and heated to reflux. After ten minutes a yellow precipitate forms and heating is continued for 2 hours. The reaction mixture is cooled, diluted with 30 ml of water, and the yellow precipitate is filtered, washed with water and dried. After chromatography over silica with dichloromethane as eluent, and recrystallization from dichloromethane and pentane, there is obtained 3.7 g (yield 63%) of yellow crystals of 5-(5-trifluoromethyl-2-furylmethylene)rhodanine. M.P. 174° C. $R_f$=0.41 with 3% methanol/dichloromethane on silica gel

| Microanalysis | C | H | N | S |
|---|---|---|---|---|
| Calculated | 38.71 | 1.44 | 5.01 | 22.96 |
| Found | 38.70 | 1.56 | 5.10 | 22.91 |

NMR spectrum in CDCl$_3$ parts per million/tetramethyl silane 6.8 multiplet (ring protons)

7.38 singlet (exocyclic methylene)

1.58 g of the above 5-(5-trifluoromethyl-2-furylmethylene)rhodanine, 23 ml of 1 N sodium hydroxide solution and 25 ml of water are stirred under nitrogen at room temperature for 10 hours. After cooling with an ice bath and acidification with concentrated hydrochloric acid to pH 1.5, the resulting slurry is filtered to yield a slightly brown precipitate which is washed with 50 ml of water by stirring at room temperature under nitrogen and filtered to yield 0.8 g of slightly brown crystals (yield 60%) of α-mercapto-β-(5-trifluoromethyl-2-furyl)-acrylic acid. M.P. 158° C.

| Microanalysis | C | H | S |
|---|---|---|---|
| Calculated | 40.34 | 2.11 | 13.46 |
| Found | 40.65 | 2.27 | 13.7 |

NMR in acetone (d 6) parts per million/tetramethylsilane
7.10 multiplet (ring protons)
7.6 singlet (exocyclic methylene)

EXAMPLE 2

α,α'-Dithiobis[β-(2-furyl)acrylic acid]

Iodine is added to a solution of 100 g of potassium iodide in 500 ml of water to saturation. This saturated solution is added dropwise to a solution of α-mercapto-β-(2-furyl)acrylic acid in 500 ml of acetonitrile and 30 ml of water until the color of iodine persists. The crude product which precipitates is recrystallized from methanol. M.P. 215° C.

EXAMPLE 3

α,α'-Dithiobis[β-(2-thienyl)acrylic acid]

Substituting α-mercapto-β-(2-thienyl)acrylic acid for α-mercapto-β-(2-furyl)acrylic acid in the procedure of Example 2 gives α,α'-dithiobis[β-(2-thienyl)acrylic acid].

EXAMPLE 4

Effects of Topically Applied α-Mercapto-β-aryl acrylic acids on Hemorrhage Caused by Snake Venoms Mice (5 per group) were injected subcutaneously with different amounts of snake venoms. Immediately after the injection and 1, 2 and 3 hours later, the mice were treated topically with ethanol (vehicle) or with 20 micromols of test compound dissolved in ethanol. Four hours after envenomation the mice were killed and skinned. Hemorrhages on the under surface of the skin and on the underlying musculature were scored on a scale of 0 to 4, according to their severity. Two observers, unaware of the treatments the animals had received, independently did the scoring; the two scores for each mouse were averaged.

| | | Mean Hemorrhagic Scores | | |
|---|---|---|---|---|
| Snake Venom | Dose of Venom (μg) | Vehicle | α-mercapto-β-(2-furyl)acrylic acid | α-mercapto-β-(2-thienyl)acrylic acid | α,α'-dithiobis[β-(2-furyl)acrylic acid] |
| Agkistrodon | 135 | 3.5 | 1.5 | | |
| contortrix | 45 | 1.9 | 0.6 | | |
| laticinctus | 15 | 1.0 | 1.0 | | |
| Agkistrodon | 45 | 2.5 | 1.1 | | |
| piscivorus | 15 | 1.6 | 0 | | |
| leukostoma | 5 | 0.9 | 0 | | |
| Agkistrodon | 135 | 4.0 | 2.3 | | |
| piscivorus | 45 | 2.7 | 0.8 | | |
| | 15 | 1.0 | 0.3 | | |
| Crotalus | 45 | 4.0 | 2.9 | | |
| adamanteus | 15 | 3.0 | 1.3 | | |
| | 5 | 1.6 | 0.2 | | |
| Crotalus | 45 | 3.0 | 1.9 | | |
| atrox | 15 | 2.0 | 0.6 | | |
| | 5 | 1.3 | 0 | | |
| Crotalus | 45 | 3.4 | 1.8 | | |
| atrox | 15 | 1.9 | 0.5 | | |
| | 5 | 1.6 | 0.5 | | |
| Crotalus | 45 | 3.2 | 1.7 | | |
| atrox | 15 | 2.2 | 0.4 | | |
| | 5 | 0.8 | 0.2 | | |
| Crotalus | 45 | 4.0 | 3.7 | | |
| cerastes | 15 | 3.4 | 2.0 | | |
| cerastes | 5 | 2.4 | 0.8 | | |
| Crotalus | 45 | 3.4 | 1.8 | | |
| horridus | 15 | 1.9 | 0.2 | | |
| horridus | 5 | 1.1 | 0 | | |
| Crotalus | 45 | 0.6 | 0.4 | | |
| scutulatus | 15 | 0.2 | 0.4 | | |
| scutulatus | 5 | 0 | 0.6 | | |
| Crotalus | 45 | 3.9 | 1.9 | | |
| viridis | 15 | 3.0 | 0.7 | | |
| helleri | 5 | 2.0 | 0.6 | | |
| Crotalus | 45 | 3.9 | 1.6 | | |
| viridis | 15 | 2.6 | 1.4 | | |
| viridis | 5 | 2.0 | 0.1 | | |
| Sistrurus | 45 | 1.9 | 1.0 | | |
| miliarius | 15 | 0.1 | 0.2 | | |
| barbouri | 5 | 0.2 | 0 | | |
| Bothrops | 25 | 3.8 | 1.0 | | |
| jararaca | 15 | 2.4 | 0.6 | | |
| | 5 | 1.6 | 0 | | |
| Bothrops | 45 | 2.9 | 2.3 | | |
| jararaca | 15 | 2.4 | 0.4 | | |
| | 5 | 1.1 | 0 | | |

-continued

| Snake Venom | Dose of Venom (μg) | Mean Hemorrhagic Scores | | | |
|---|---|---|---|---|---|
| | | Vehicle | α-mercapto-β-(2-furyl)acrylic acid | α-mercapto-β-(2-thienyl)acrylic acid | α,α'-dithiobis[β-(2-furyl)acrylic acid] |
| Lachesis | 50 | 2.7 | 1.8 | | |
| mutus | 17 | 1.6 | 1.0 | | |
| | 6 | 0.9 | 0.4 | | |
| Trimeresurus | 45 | 2.3 | 1.2 | | |
| flavoviridis | 15 | 2.1 | 0.1 | | |
| | 5 | 1.0 | 0.1 | | |
| Bitis | 15 | 3.3 | 2.0 | | |
| arietans | 5 | 3.3 | 0.8 | | |
| | 1.7 | 1.7 | 0 | | |
| Bitis | 9 | 3.7 | | 2.3 | 2.6 |
| arietans | 3 | 2.5 | | 1.2 | 1.9 |
| | 1 | 1.4 | | 0.1 | 0.8 |
| Echis | 50 | 3.4 | 2.4 | | |
| carinatus | 17 | 2.7 | 2.0 | | |
| | 6 | 0.6 | 1.0 | | |
| Vipera | 100 | 2.8 | 1.9 | | |
| russelli | 33 | 1.6 | 1.1 | | |
| | 11 | 0.6 | 0.9 | | |

EXAMPLE 5

Mice (5 per group) were injected subcutaneously with 5 ug of Bitis arietans venom. Immediately after injection and 1 hour later, the mice were treated topically with ethanol (control) or with 20 micromols of α-mercapto-β-(2-furyl)acrylic acid dissolved in ethanol. Four hours after envenomation the mice were killed and skinned. Mean Hemorrhagic Scores were determined as in Example 4. The Score for the acrylic acid was found to be 1.2 as compared with the control score of 3.1.

EXAMPLE 6

Mice (5 per group) were injected with different amounts of Bitis arietans venom. Immediately after the injection the mice were treated orally with 50% propylene glycol (vehicle) or with α-mercapto-β-(2-furyl)acrylic acid (50 mg/kg) dissolved in 50% propylene glycol. Mean Hemorrhagic Scores were determined as in Example 4.

| Dose of Venom (μg) | Mean Hemorrhagic Scores | |
|---|---|---|
| | Vehicle | α-mercapto-β-(2-furyl)acrylic acid |
| 9 | 3.6 | 2.6 |
| 3 | 2.2 | 1.0 |
| 1 | 2.2 | 0.4 |

I claim:

1. A method of reducing local hemorrhage and tissue necrosis in mammals resulting from the bite or sting of a venomous snake which comprises administering to said mammal a local hemorrhage and tissure necrosis reducing amount of a compound having the formula

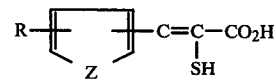

or a corresponding disulfide of the formula

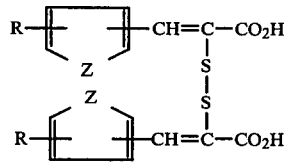

wherein Z is S and R is selected from the group consisting of H, methyl, ethyl, hydroxy, methoxy, ethoxy, fluoro, chloro, bromo, iodo and trifluoromethyl; or a pharmaceutically acceptable salt thereof.

2. A method of claim 1 wherein the compound is administered topically.

3. A method of claim 1 wherein the local hemorrhage and tissue necrosis results from the bite of a venomous pit viper.

4. A method of claim 1 wherein the mammal is a human.

5. A methods of claim 1 wherein the compound is α-mercapto-β-(2 thienyl)acrylic acid or a pharmaceutically acceptable salt thereof.

6. A method of claim 1 wherein the compound is α,α'-dithiobis[β-(2-thienyl)acrylic]acid or a pharmaceutically acceptable salt thereof.

* * * * *